United States Patent [19]

Calenoff et al.

[11] Patent Number: 4,849,337
[45] Date of Patent: Jul. 18, 1989

[54] ASSAYING ALLERGEN SPECIFIC IGE LEVELS WITH FLUOROGENIC ENZYME LABELED ANTIBODY

[75] Inventors: Emanuel Calenoff, Burlingame; Ruth M. Jones, Los Altos; Yuh-Geng Tsay, San Jose; John R. Scott, Mountain View, all of Calif.

[73] Assignee: Minnesota Mining and Manufacturing Company, St. Paul, Minn.

[21] Appl. No.: 144,730

[22] Filed: Jan. 14, 1988

Related U.S. Application Data

[63] Continuation of Ser. No. 462,585, Jan. 31, 1983, abandoned, which is a continuation-in-part of Ser. No. 444,622, Nov. 26, 1982, abandoned, which is a continuation-in-part of Ser. No. 434,061, Oct. 13, 1982, abandoned.

[51] Int. Cl.$^4$ .................... G10N 33/53; G10N 33/577
[52] U.S. Cl. .......................................... 435/7; 435/21; 436/513; 436/532; 436/548; 436/809
[58] Field of Search ...................... 435/7, 21; 436/513, 436/809, 532, 548

[56] References Cited

U.S. PATENT DOCUMENTS

| | | | |
|---|---|---|---|
| 3,720,760 | 3/1973 | Bennich | 424/1 |
| 3,941,876 | 3/1976 | Marinkovich | 424/1 |
| 4,002,532 | 1/1977 | Weltman | 436/513 X |
| 4,211,762 | 7/1980 | Huggins et al. | 424/1 |
| 4,240,751 | 12/1980 | Linnecke | 435/251 |
| 4,331,650 | 5/1982 | Brewer | 424/12 |
| 4,347,311 | 8/1982 | Schmitz | 435/5 |
| 4,376,110 | 3/1983 | David | 436/548 |
| 4,410,634 | 10/1983 | Cooper et al. | |
| 4,501,970 | 2/1985 | Nelson | |

FOREIGN PATENT DOCUMENTS 83306178.1 10/1982 European Pat. Off. .

OTHER PUBLICATIONS

Chemical Abstracts, 99:156476q (1983).
"Automated Immunoanalysis", Part 2, R. F. Ritchie, ed., pp. 335-342, Marcel Dekker, Inc., New York, 1978.
"Enzyme-Immunoassay", Maggio, E. T., ed., pp. 26, 173-178, 186, CRC Press, Inc., Boca Raton, 1980.
King, Te Piao et al, Skandia Int. Symp. 1982(1983) 15th (Theor. Clin. Aspects Allerg. Dis), 215-36.
Shalev, A, et al; J. Immunol. Methods, 38:125-139 (1980).
Voller, A, et al; Brief Communication, WHO 51:209-211 (1974).
Hill, P., et al; J. Immunol. Meth.; 45:51-63 (1981).
Hellsing, k., et al Chapt. 3, pp. 67-112 Automated Immunoanalysis (Marcel Dekker, New York).
Ceska, M., et al, Eur. J. Immunol. 2:58-62 (1972).
Butler, J. E., Chapt. 2 "Antibody-Antigen and Antibody-Hapten Reactions", pp. 5-52 in *Enzyme Immunoassay*, (E. Maggio, Ed CRC Press Buca Raton, Fla. 1980).
Clark, B. et al Chapt. 8 "Enzyme Linked Immunosorbent Assay (ELISA): Theoretical and Practical Aspects" pp. 167-179 in *Enzyme Immunoassay* (E. Maggio, Ed. CRC Press Boca Raton, Fla (1980).
Mattiasson, B., et al Chapt. 11 "Novel Approaches to Enzyme Immunoassay" pp. 213-248 in *Enzyme Immunoassay* (E. Maggio, Ed CRC Press Boca Raton, Fla. 1980).
Savory, J., et al Chapt. 16 pp. 335-343 in Automated Immunoanalysis Part 2 (R. Ritchie, and Marcel Dekker, Inc. New York 1978).
Voller, A., Chapt. 9 "Heterogenaous Enzyme-Immunoassays are the Applications" pp. 181-196 in *Enzyme Immunoassay* (E. Maggio, ed CTC Press, Boca Ration, Fla 1980).

*Primary Examiner*—Christine M. Nucker
*Attorney, Agent, or Firm*—Donald M. Sell; Walter N. Kirn; Philip M. Goldman

[57] ABSTRACT

A method for identifying and quantifying allergen specific IgE levels in patent serum by conjugating the IgE in the serum with allergens adhering to an insoluble support, conjugating the serum IgE with an enzyme labeled anti-IgE antibody, contacting the enzyme label with a solution of a substrate which will yield a fluorescent product in the presence of the enzyme, and measuring the level of fluorescence in the solution. Special reagents and their manufacture are also disclosed.

20 Claims, No Drawings

ASSAYING ALLERGEN SPECIFIC IGE LEVELS WITH FLUOROGENIC ENZYME LABELED ANTIBODY

RELATIONSHIP TO COPENDING APPLICATIONS

This is a continuation of Ser. No. 462,585, filed Jan. 31, 1983, now abandoned, which is a continuation-in-part of application Ser. No. 444,622 filed Nov. 26, 1982, now abandoned, which is, in turn, a continuation-in-part of application Ser. No. 434,061 filed Oct. 13, 1982.

FIELD OF THE INVENTION

This invention relates to methods and reagents for assaying blood serum of patients demonstrating allergic symptomotology to identify the source of the allergy and determine the level of the respective allergen specific IgE in the serum. In particular, this invention relates to diagnostic methods and reagents therefor which provide increased specificity and accuracy, the results of which can be reliable used as a basis for determining desensitization dose regimens to be used in treating patients for allergic reactions.

BACKGROUND OF THE INVENTION

Description of the Prior Art

Radiometric and fluorometric methods for identifying and measuring allergy specific IgE levels in patient serum are commercially available and are known as the RAST test, for example. U.S. Pat. Nos. Re. 29,474; 3,555,143; 3,648,346; 3,720,760 and 3,966,898 relate to these methods and reagents therefor. Enzymatic immunological methods for identifying and quantifying antigens and antibodies in liquids are widely used and are known as the ELISA and EIA, for example. Basic technology for enzymatic assays and reagents therefor is disclosed in U.S. Pat. Nos. Re. 29,169 and 3,839,153, for example.

A review of the current state of the art with regard to immunoassays for the detection of proteins in solutions is provided by R. Rose et al, *Manual of Clinical Immunology*, 2nd ed. American Society for Microbiology, Washington, pp 327–429, 775–849 (1980) and by A. Voller et al, *Immunoassays for the 80's*, University Park Press, Baltimore (1981), and the publications cited therein, the entire contents of both publications being hereby incorporated by reference. The chapter therein by T. A. E. Platts-Mills et al, "Radioimmunoassays in Allergy", pp 289–311, and the publications cited therein provide a comprehensive review of the field of this invention.

Procedures for binding proteins to insoluble supports have been primarily described. Antibodies have also been covalently bonded to insoluble supports as described in U.S. Pat. Nos. 3,551,555, 3,553,310, 4,048,298 and RE-29,474. Binding of antibodies to polystyrene by adsorption has been described in U.S. Pat. Nos. 3,646,346 and 4,092,408, for example. Allergens have been covalently bonded to a variety of insoluble supports as described in U.S. Pat. No. 3,720,760.

Polyethylene glycol has been used in protein fractionation processes as described by A. Polson et al, *Biochim. Biophys Acta*, vol. 82, pp 463–475 (1964) and A. Polson et al, *Vox Sang*, vol. 23, pp. 107–118 (1972).

SUMMARY OF THE INVENTION

This invention relates to a method for identifying and quantifying allergen specific IgE levels in patient serum. It comprises the steps of first contacting an insoluble support having allergen adhering thereto with patient serum for a sufficient time to permit conjugation of allergen with IgE in the patient serum. The patient serum is then removed from the support. Secondly, the insoluble support is contacted with an anti-IgE antibody labeled with a fluorogenic enzyme for sufficient time to permit conjugation of serum IgE conjugated with allergen on the insoluble support with the anti-IgE antibody. A fluorogenic enzyme, as used herein, is defined as an enzyme by means of which suitable substrate will undergo chemical reaction to yield fluorescent products. The unconjugated anti-IgE antibody is then removed from the support. Thirdly, the insoluble support is contacted with a solution of a substrate which undergoes chemical reaction to yield a fluorescent product when in the presence of the fluorogenic enzyme, the contact being continued for a sufficient time to yield fluorescent product. The level of fluorescence in the solution is then measured.

In the insoluble allergen reagent of this invention the allergen is preferably adherent to the insoluble support by non-covalent bonding such as by absorption or adsorption, for example. The allergen adhering to the insoluble support is preferably present as a novel intermediate of this invention comprising an allergen covalently bonded to a water-soluble polymer having an absorption or adsorption affinity for the insoluble support. The allergen-polymer product is adherent to the insoluble support by non-covalent bonding.

In certain preferred embodiments of this invention, the insoluble support has a plurality of test wells separated by opaque material, the anti-IgE antibody is a monoclonal antibody to which alkaline phosphatase is bound, the anti-IgE is contacted with the insoluble support in an aqueous solution containing from 1 to 8 weight percent polyethylene glycol having a molecular weight of from 1000 to 10,000 and a non-ionic surfactant, and the substrate is 4-methylumbelliferyl phosphate. If the allergen bonded to the insoluble support is covalently bonded to a water-soluble polymer having absorption or adsorption affinity for the insoluble support, in a preferred procedure the insoluble support is prerinsed with an aqueous buffered rinse solution containing from 0.0001 to 0.5 weight percent of the water-soluble polymer.

DETAILED DESCRIPTION OF THE INVENTION

Key to successful treatment of allergic conditions is the accurate identification of the offending allergen and the titration of the patient to determine the desensitization dosage. In general, reconstituted allergen extract is injected in sufficient quantity to cause major production of antigen-specific IgG (blocking antibody) and major production and/or activation of suppressor T lymphocytes. However, the quantity should not be sufficient to cause major allergic reaction. To the extent that antigen-specific IgE is produced at an increased level, it is critical that the IgG and suppressor IgE production be in such balance as to prevent allergic reaction.

The concentration and amount of the desensitization dosage are dependent upon many factors which are specific to the patient undergoing the allergic reaction.

It is, therefore, necessary to titrate the patient to determine the proper dosage. A variety of standard techniques are available to carry out this procedure. Examples of traditional procedures are described in *Remington's Pharmaceutical Sciences*, supra, pp 1344–1352, the entire contents of which are incorporated herein by reference. However, the methods available prior to this invention have lacked the specificity and accuracy to be more than a rough approximation of the order of magnitude of the appropriate beginning dose range.

The method of this invention provides the specificity and accuracy to determine a suitable desensitization dosage, particularly when the allergen used for desensitization and the allergen component of the diagnostic method have the same allergen profile and specificity. After identification of the offending allergen and quantification of the offending allergen, standard desensitization immunotherapy procedures are employed. The procedure normally used involves injecting into the patient gradually increased doses of the allergen, usually to maximum tolerated doses (doses not giving rise to major allergic response), at varying intervals in an attempt to develop IgG antibody protection against the agents and to increase the specific suppressor T lymphocyte activity. With the method of this invention, more exact assessment of the suitable desensitization dose can be initially determined, making unnecessary the exacting procedures formerly required. The exact mechanisms of this treatment are not fully understood. Booster injections to maintain the requisite IgG and suppressor T lymphocyte levels are required at intervals of one to four weeks. Usually the doses required for booster injections are substantially greater than the maximum dose required for control of the initial allergic reaction.

The process of this invention comprises a first step of contacting an insoluble support having allergen adhering thereto with patient serum for a sufficient time to permit conjugation of allergen with IgE in the patient serum and then removing the patient serum from the support. In this procedure the patient serum is preferably undiluted prior to contact with the supported allergen. The incubation time should be sufficient to permit substantial conjugation to occur, the time being temperature dependent. Suitable incubation times are from 30 to 180 minutes at temperatures within the range of from 18° to 40° C., the preferred contact time being from 60 to 120 minutes at temperatures within the range of from 20° to 26° C.

The insoluble support having the allergen adhering thereto is an important aspect of this invention. The allergen can be any allergenic material such as allergen derived from pollens derived from trees, shrubs, weeds, and grasses; molds; smuts; dusts; allergens derived from danders, hair, and epidermals of animals; extracts derived from insects including insect venoms; and from foods.

A wide variety of compounds can be employed as the solid support, the primary consideration being the binding of the allergens to the surface, the absence of interference with the enzyme labeled anti-IgE antibody reagent, enzymatic reaction thereof with a substrate and fluorescent properties of the enzymatic reaction product. Organic and inorganic polymers, both natural and synthetic can be employed as the solid support. Examples of suitable polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, styrene-acrylonitrile copolymers, rayon, nylon, polyvinylbutyrate, polyformaldehyde, etc. Other materials which can be employed as the insoluble support are silica gel, silicon wafers, glass, paper, insoluble protein, metals, metaleoids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12–24 carbon atoms) alkyl ammonium salts and the like.

A preferred diagnostic support of this invention comprises a polystyrene, styrene copolymers including styrene-(vinyl monomer) copolymers such as styrene-acrylonitrile copolymers, or polyolefins such as polyethylene and polypropylene, and acrylate and methacrylate polymers and copolymers. The allergenic extract is preferably bound thereto by adsorption, ionic bonding, van der Waals adsorption, electrostatic bonding, other non-covalent bonding. It can also be bound to the support by covalent bonding. A particularly advantageous support for this procedure comprises a microtiter plate having a plurality of wells. The well surface or plastic cup inserts therein can constitute the allergen support. Most advantageously, the microtiter plate or the well inserts are opaque to light so that excitation light applied to a well or fluorescence generated in response thereto does not reach or influence contents of the surrounding wells. With this system each well can be employed as a test system independent of the other wells.

Preferably the allergen is covalently bonded to a water-soluble polymer having an affinity for the insoluble substrate. The allergen-polymer product is then adhered to the insoluble substrate by non-covalent bonding such as by adsorption or absorption.

Suitable water-soluble proteins include bovine serum albumins of bovine (BSA), human (HSA), rabbit (RSA), goat (GSA), sheep (SSA), horse (HOSA), etc.; serum gamma Globulin of the previously described animals; and other animal proteins such as ovalbumin, fribrinogen, thrombin, transferin, glycoproteins, etc. Suitable water-soluble amino acid polymers include polylysine, polyglutamic acid, polyalanine, polyhistidine, polymethionine, polyproline, etc. The allergen can be covalently bonded to water-soluble protein or amino acid polymer with conventional coupling agents using methods which are known in the art. Preferably the coupling agent is a carbodiimide such as 1-ethyl-3-(3-N,N-dimethylaminopropyl)carbodiimide hydrochloride and 1-cyclohexyl-3(2-morpholinoethyl) carbodiimide methyl-p-toluenesulfonate. Other suitable coupling agents include aldehyde coupling agents having either ethylenic unsaturation such as acrolein, methacrolin, or 2-butenal or having a plurality of aldehyde groups such as glutaraldehyde, propanedial or butanedial. Other coupling agents include bifunctional NHS-esters such as disuccinimidyl suberate, disuccinimidyl tartarate, bis[2-(succinimidooxycarbonyloxy)ethyl]sulfone, disuccinimidyl (N,N'-diacetylhomocystine, dithiobis(succinimidyl propionate), ethylene glycolbis(succinimidyl succinate); heterobifunctional reagents such as N-5-azido-2-nitrobenzoyloxy succinimide, p-azidophenacyl bromide, p-azidophenylglyoxal, 4-fluoro-3-nitrophenyl azide, N-hydroxysuccinimidyl-4-azidobenzoate, m-maleimidobenzoyl N-hydroxysuccinimide ester, methyl-4-azidobenzoimidate.HCl, p-nitrophenyl 2-diazo-3,3,3-trifluoropropionate, N-succinimidyl-6(4'-azido-2'-nitrophenylamino)hexanoate, succinimidyl 4-(N-maleimido-methyl)cyclohexane-1-carboxylate, succinimidyl 4-(p-maleimidophenyl)butyrate, N-succinimidyl (4-azidophenyldithio)propionate, N-succinimidyl 3-(2-pyridyldithio)propionate, N-(4-azidophenylthio)phthalimide, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonyl-bis(L-methionine p-nitrophenyl ester), 4,4'-dithiobisphenylazide, erythritolbiscarbonate; and bifunctional imidoesters such as dimethyl adipimidate.2HCl, dimethyl suberimidate, dimethyl 3,3'-dithiobispropionimidate.2HCl, 2-iminothiolane.HCl, covalent bonding of allergen to the insoluble protein can be carried out with the above reagents by conventional, well-known reactions, for example in the aqueous solutions at a neutral pH, at temperatures of less than 10° C. for 18 hours or overnight.

In a procedure for non-covalent adhesion of allergen to the surface of an insoluble support, the allergenic material can be applied to the surface of a support such as a polystyrene microtiter well or polystyrene individual insert well therefor, in an aqueous buffer solution. The surface is initially cleaned with a cleaning fluid such as methanol and dried. The buffered allergen solution is placed in the well or insert cup and incubated at room temperature until adsorption occurs, for example for from 2 to 18 hours and preferably from 16–18 hours, at temperatures of from 4° to 40° C. and preferably from 20° to 26° C. The well is then rinsed with a weak saline solution and dried. Other procedures for covalently adhering allergens to insoluble supports are described by Ichiro Chibata in *Immobilized Enzymes*, Halsted Press, New York, 1978, and by A. Cuatrecasas, *J. Bio. Chem.* 245 3059(1970), the entire contents of which are hereby incorporated by reference. The surface can be coated with a protein and coupled with allergen using the procedures described in U.S. Pat. No. 4,210,418 using glutaraldehyde as a coupling agent, for example. In a still further procedure, the well can be coated with a layer having free isocyanate groups such as a polyether isocyanate, and application of the allergen in aqueous solution thereto effects the requisite bonding. In a still further procedure, the allergen can be coupled to a hydroxylated material by means of cyanogen bromide as described in U.S. Pat. No. 3,720,760.

Preferred allergens are those described in commonly assigned copending patent application Ser. No. 433.962 filed Oct. 13, 1982, the entire contents of which are incorporated by reference.

If the allergen is covalently bonded to a water-soluble polymer having an affinity for the insoluble substrate and the water-soluble polymer has antigenic properties, the first step is preferably preceded by a prerinse step. In the prerinse step, the support surface is contacted with an aqueous buffered rinse solution containing from 0.0001 to 0.5 weight percent of the water-soluble antigenic polymer to which the allergen is bound. This prerinse step is particularly advantageous when the water-soluble polymer is water-soluble animal protein because rinse residue will provide a sufficient amount of the water-soluble protein to conjugate with any of the protein-specific IgE which is present in the patient serum. The protein-specific IgE would otherwise complex with the protein on the insoluble support as a non-specific IgE binding, greatly reducing the sensitivity of the assay.

A preferred rinse solution of this invention is an aqueous phosphate buffer solution having a phosphate molarity of from 0.01 to 0.05, a pH of from 6 to 8 and containing from 0.01 to 0.01 weight percent non-ionic surfactant and from 0.0001 to 0.5 weight percent of the antigenic protein to which the allergen is coupled. Suitable non-ionic surfactants include polyoxyethylene ethers (BRIJ ®) such as lauryl, cetyl, oleyl, stearyl, and tridecyl polyoxyethylene ethers; polyoxyethylenesorbitans (TWEEN ®) such as polyoxyethylenesorbitan monolaurate, monopalmitate, monostearate, monoleate and trioleates; and other polyoxyethylene ethers (TRITON ®), for example. A preferred non-ionic surfactant is octylphenoxypolyethoxy ethanol having 40 ethylene oxide units (TRITON X-405, Rohm and Haas Company.

The buffer solution is advantageously prepared from a reagent concentrate of the invention comprising from 0.005 to 2.5 weight percent of the animal protein corresponding to the animal protein to which the allergen is covalently bonded, from 0.5 to 5 weight percent non-ionic surfactant, from 10 to 20 weight percent sodium chloride, from 0.5 to 5 weight percent stabilizer and sufficient phosphate salt to provide for a 0.02 to 0.05 M phosphate solution. The pH can be from 6 to 8. The preferred buffer concentrate contains about 0.5 weight percent of the animal protein, 0.1 weight percent TRITON X-405 non-ionic surfactant, 17 weight percent sodium chloride, and 2 weight percent sodium azide, 0.01 M phosphate and has a pH of 7.4.

After conjugation of serum IgE with allergen adhering to the insoluble support has occurred, the patient serum is removed therefrom. Surplus liquid is removed and the solid surface is then rinsed with a suitable rinse solution such as that described above.

The second step of the process of this invention comprises contacting the insoluble support with an anti-IgE antibody labeled with a fluorogenic enzyme. The incubation is continued for sufficient time to permit serum IgE conjugated with allergen (if any) on the insoluble support to conjugate with the anti-IgE antibody. After incubation, the excess liquid is removed, and the surface of the insoluble support is rinsed with a weak saline solution as described above with respect to the first step to remove unconjugated antibody. Preferably the support is rinsed with the preferred rinse solution of this invention described above.

Anti-IgE antibodies are available from many sources, and the methodology for producing them is well known and is described in several of the patents and publications cited above. The preferred antibodies are monoclonal antibodies. The technology for making monoclonal antibodies is well developed, and the procedures suitable for making monoclonal anti-IgE antibodies are described by D. Catty, et al in "Antisera in Immunoassays with special Reference to Monoclonal Antibodies to Human Immunoglobulins", *Immunoassay's for the 80's*, supra, pp 133–153 and the publications cited therein, the entire contents of which are hereby incorporated by reference.

Fluorogenic enzymes and methods for bonding them to antibodies without impairing the ability of the antibody to selectively conjugate with antigen are well known in the art. Suitable enzymes and procedures for coupling them to antibodies are described in U.S. Pat. No. 4,190,496, for example, the contents thereof being hereby incorporated by reference. The preferred fluorogenic enzymes and the suitable substrates corresponding thereto include horse-radish peroxidase for which a suitable substrate is homovanillic acid or 4-hydroxy-3-methoxyphenylacetic acid, beta-galactosidase for which a suitable substrate is 4-methylumbelliferyl-beta-D-Galactoside, alkaline phosphatase for which a suitable substrate is 4-methylumbelliferyl phosphate and other umbelliferyl phosphates such as 4-carboxyumbellifery phosphate, and umbelliferyl phosphate 4-carboxy alkylesters, etc.

Examples of suitable procedures for enzyme labeling the anti-IgE antibody include carbodiimides, dialdehyde, and bifunctional coupling reagents as described in covalent linkage of allergen to water-soluble polymer or periodate coupling where enzyme has glycoprotein moiety.

The enzyme labeled anti-IgE antibody is applied to the insoluble support in an aqueous solution. The solution preferably contains suitable salts and buffers to preserve the reactants and facilitate the conjugation reaction. For example, the solution can contain bovine serum albumin (BSA), phosphate buffer solution (PBS), and a mild surfactant such as a polyoxyethylene sorbitan ester employed in the rinse solutions described above. The rinse solutions described hereinabove can also be used.

A preferred solution of this invention comprises from 0.1 micrograms per ml to 5 micrograms per ml and preferably from 1 microgram per ml to 2 microgram per ml anti-IgE antibody in an aqueous phosphate buffered solution having a phosphate molarity of from 0.005 to 0.1 and preferably from 0.01 to 0.05 and a pH of from 6.0 to 8.0 and preferably 7.2 to 7.6. A critical ingredient in the anti-IgE solution is polyethylene glycol having molecular weights of from 1000 to 8000 and preferably from 2000 to 4000 in concentrations of from 1 to 8 and preferably from 2 to 6 weight percent. Polyethylene glycols greatly increase the speed and sensitivity of the reaction. Another important ingredient is a non-ionic surfactant in concentrations of from 0.01 to 0.5 and preferably from 0.02 to 0.1 weight percent. Suitable non-ionic surfactants include those described above with respect to rinse solutions, for example. A preferred non-ionic surfactant is TRITON X-405. The surfactant surprisingly reduces the non-specific background fluorescence signal in the assay.

With the preferred anti-IgE solutions of this invention, the incubation time of the solutions with the insoluble support is temperature dependent. At temperatures of 18° to 40° C., incubation times of at least from 30 to 180 minutes can be used. The preferred temperatures are within the range of from 20° to 26° C., and at these temperatures, incubation times from 60 to 120 minutes can be employed. It should be appreciated that prolonged incubation times in any of the steps of this invention can reduce the efficacy of the process. Since rapid analysis is an objective of this invention, the lowest times which still yield the desired accuracy are preferred.

The solid support is then rinsed to remove residual, unconjugated enzyme labeled anti-IgE antibody. The rinse solutions described above are suitable.

The third step of the process of this invention comprises contacting the solid support with a solution of a substrate which undergoes chemical reaction in the presence of the fluorogenic enzyme for a time sufficient for fluorescent compounds to be formed. Suitable substrates and the enzymes they are converted by are known in the art and are described in U.S. Pat. No. 4,190,496, for example. Examples of substrates have been described hereinabove with respect to the corresponding fluorogenic enzyme.

The solid is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reaction product to form. At temperatures of from 18° to 40° C., incubation times of from 5 to 240 minutes can be used. Preferably, the temperature is within the range of from 20° to 26° C., and the incubation time is from 30 to 90 minutes.

The equipment and procedures for determining the level of fluorescence in the substrate solutions are those conventionally employed in the art. The level of fluorescence is a function of the enzyme concentration on the insoluble support which is, in turn, a function of the allergen specific IgE level in the patient serum. By comparing the fluoresence level with the levels measured by carrying out the procedure with control solutions containing known concentrations of the respective allergen specific IgE, the precise concentration of the corresponding IgE antibody in the patient serum can be determined.

Suitable fluorometers are the fluorometers by Perkin-Elmer, American Instrument Company, and Turner Designs. The Allergenetics Fluorometer (Allergenetics, Inc., Mountain View, Calif.) is preferred.

This invention is further illustrated by the following specific but non-limiting examples. Temperatures are given in degrees Centigrade and concentrations are given as weight percents unless otherwise specified.

EXAMPLE 1

To a solution of timothy grass pollen allergen extract (3 mg/ml) was added 10 microliters of a 5 wt/% bovine serum albumin (BSA) solution. After addition, the solution was kept at 4° C., and 5 mg of 1-Ethyl-3-(3-N,N-Dimethylaminopropyl) carbodiimide (ECDI) was added. The mixture was gently stirred at 4° C. for 20 minutes. The additions of both BSA and ECDI were repeated three more times. The final mixture was allowed to stand at 4° C. overnight to yield a conjugate of timothy grass pollen allergen covalently bonded to BSA.

EXAMPLE 2

The procedure of Example 1 was repeated, replacing the timothy grass pollen extract with the following allergenic extracts: Grasses - Bermuda Grass, *Cynodon dactylon*, Orchard Grass, *Dactylis glomerata*, Perennial Rye Grass, *Lolium perenne*, June Grass (Kentucky Blue), *Poa pratensis*, Bent Grass, *Agrostis maritima*, Johnson Grass, *Sorghum halepense*, Brome Grass,

*Bromus inermis*, Bahia Grass, *Paspalum notatum*, Corn Grass, *Zea mays*, Meadow Fescue, *Festuca elatior*, and Redtop, *Agrostis alba*; Weeds - Short Ragweed, *Ambrosia artemisifolia*, Western Ragweed, *Ambrosia psilostachya*, False Ragweed, *Franseria acanthicarpa*, Sagebrush (common), *Artemisia tridentata*, Dandelion, *Taraxacum vulgare*, English Plantain, *Plantago lanceolata*, Lamb's Quarters, *Chenopodium album*, Russian Thistle, *Salsola kali*, Goldenrod, Solidago sp., Pigweed, *Amaranthus retroflexus*, Dock (yellow), *Rumex crispus*, and Sheep Sorrel, *Rumex acetosella*; Trees - Box Elder (Maple), *Acer negundo*, Alder, *Alnus rhombifolia*, Birch, *Betula nigra*, Mountain Cedar, *Juniperus sabinoides*, White Oak, *Quercus alba*, Elm, *Ulmus americana*, Olive, *Olea europaea*, Black Walnut, *Juglans nigra*, Sycamore, *Platanus occidentalis*, Cottonwood, *Populus trichocarpa*, White Ash, *Fraxinus americana*, White Pine, *Pinus monticola*, Eucalyptus, Eucalyptus sp., Acacia, *Acacia baileyana*, Aspen, *Populus tremuloides*, Arizona Cypress, *Cupressus arizonica*, Mesquite, *Prosopis juliflora*, Privet, *Ligustrum ovalifolium*, Melaleuca (Punk Tree), *Melaleuca leucadendron*, and Australian Pine (Beefwood), *Casuarina equisetifolia*; Epidermals - Cat Epithelium, Dog Hair and Dander, Horse Hair and Dander, Cow Hair and Dander, Guinea Pig Hair and Dander, Feather Mix (Chicken, Duck and Goose), and Wool (Sheep); Molds -*Penicillium notatum*, Cladosporium herbarum, Aspergillus fumigatus, Mucor racemosus, Candida albicans, and *Alternaria tenuis*; House Dust; Mite - *Dermatophagoides farinae*; and Foods - Milk, Wheat, Corn, Rice, Peanut, Soybean, Shrimp, Tomato, Pork, Carrot, Orange, Potato, Tuna, Beef, Lamb, Chicken, Whole Egg, Yeast (Bakers), Sweet Potato, Cabbage, Lettuce, Pepper (Bell), Apple, Cranberry, Grape, Barley, and Onion. This yielded the corresponding, respective, covalently bonded BSA conjugate of each allergen.

EXAMPLE 3

Repeating the procedure of Example 1 but replacing the timothy grass pollen extracts with extracts of the following tree pollens yields the corresponding, respective covalently bonded BSA-allergen conjugates: Acacia -*Acacia longifolia*; Ailanthus (See Tree of Heaven) - *Ailanthus altissima*; Alder, Mountain (Tag) (Slender) - *Ainus tenuifolia/ incana*; Alder, Red (Oregon) - *Alnus rubra*; Alder, Sitka - *Alnus sinuata*; Almond - *Prunus amygdalus*; Apple - *Pyrus malus (Malus pumila)*; Apricot - *Prunus armeniaca*; Arbor Vitae, Oriental (Ornamental) - *Betula papyrifera*; Birch, Spring - *Betula fontinalis*; Birch, White (Weeping) - *Betula pendula*; Birch, Yellow - *Betula lutea*; Blue Beech (Am. Hornbeam) - *Carpinus carolineana*; Bottle Brush - *Callistemon citrinus*; Butternut - *Juglans cinerea*; Carob Tree - *Ceratonia siliqua*; Cedar, Deodar -*Cedrus deodora*; Cedar, Giant - *Thuja plicata*; Cedar, Incense - *Linocedrus decurrens*; Cedar, Japanese -*Cryptomeria japonica*; Cedar, Port Orford (Lawson Cypress) -*Chamaecyparis lawsoniana*; Cedar, Red - *Juniperus virginiana*; Cedar, Rocky Mountain - *Juniperus scopulorum*; Cedar, Salt (Tamarisk) - *Tamarix gallica*; Cedar, White - *Thuja occidentalis*; Cherry, *Prunus cerasus*; Chestnut, American -*Castanea dentata*; Chestnut, Horse - *Aesculus hippocastanum*; Cottonwood, Common - *Populus deltoides*; Cottonwood, Fremont - *Populus fremontii*; Cypress, Bald (White) -*Taxodium distichum*; Cypress, Italian - *Cupressus sempervirens*; Cypress, Monterey - *Cupressus macrocarpa*; Elderberry -*Sambucus glauca*; Elm, Cedar (Fall Blooming) - *Ulmus crassifolia*; Elm, Chinese - *Ulmus parvifolia*; Elm, Siberian -*Ulmus pumila*; Elm, Slippery - *Ulmus fulva* (rubra); Fir, Douglas - *Pseudotsuga menziesii*; Fir, Red (Noble) - *Abies nobilis (procera)*; Fir, White - *Abies concolor*; Gum, Sweet -*Liquidambar styraciflua*; Hackberry - *Celtis occidentalis*; Hazelnut, American - *Corylus americana*; Hemlock, Eastern -*Tsuga canadensis*; Hemlock, Western - *Tsuga heterophylla*; Hickory, Shagbark - *Carya ovata*; Hickory, Shellbark -*Carya laciniosa*; Hickory, White - *Carya tomentosa*; Ironwood (Hop-Hornbeam) - *Ostrya virginiana*; Juniper, California - *Juniperus californica*; Juniper, Chinese -*Juniperus chinensis*; Juniper, Oneseed - *Juniperus monosperma*; Juniper, Pinchot - *Juniperus pinchotti*; Juniper, Utah -*Juniperus osteosperma (juniperus utahensis)*; Juniper, Western - *Juniperus occidentalis*; Lilac - *Syringa vulgaris*; Linden (Basswood) - *Tilia americana*; Locust, Black -*Robinia pseudoacacia*; Maple, Big-Leaf (Coast) - *Acer macrophyllum*; Maple, Hard (Sugar) - *Acer saccharum*; Maple, Red - *Acer rubrum*; Maple, Soft (Silver) - *Acer saccharinum*; Mock Orange, Wild (Syringa) - *Philadelphus lewisii*; Mulberry, Paper - *Broussonetia papyifera*; Mulberry, Red - *Morus rubra*; Mulberry, White - *Morus alba*; Oak, Arizona (Gambel) - *Quercus gambelii*; Oak, Arizona Scrub (Canyon) - *Quercus chrysolepsis*; Oak, Black (Yellow) -*Quercus velutina*; Oak, Black Jack - *Quercus marilandica*; Oak, Bur - *Quercus macrocarpa*; Oak, California Black -*Quercus kelloggii*-californica; Oak, California Scrub -*Quercus dumosa*; Oak, Coast Live - *Quercus agrifolia*; Oak, Engelmann - *Quercus engelmanii*; Oak, Garry (Western White) -*Quercus garryana*; Oak, Holly - *Quercus ilex*; Oak, Interior Live - *Quercus wislizenii*; Oak, Post - *Quercus stellata*; Oak, Red - *Quercus rubra*; Oak, Swamp (Pin) - *Quercus palustris*; Oak, Valley - *Quercus lobata*; Oak, Virginia Live - *Quercus virginiana*; Oak, Water - *Quercus nigra*; Olive - *Olea europaea*; Orange - *Citrus sinensis*; Osage Orange - *Maclura pomifera*; Palm, Date - *Phoenix dactylifera*; Palm, Dwarf - *Chamaerops humulis*; Palm, Canary Island Date (Ornamental) - *Phoenix canariensis*; Palm, Queen - *Cocos plumosa*; Peach - *Prunus persica*; Pear - *Pyrus communis*; Pecan - *Carya pecan*; Pepper Tree, California - *Schinus molle*; Pepper Tree, Brazilian - *Schinus terebinthifolius*; Pine, Austrian - *Pinus nigra*; Pine, Canary Island - *Pinus canariensis*; Pine, Digger - *Pinus sabiniana*; Pine, Loblolly - *Pinus taeda*; Pine, Lodgepole - *Pinus contorta*; Pine, Monterey - *Pinus radiata*; Pine, Pinyon - *Pinus edulis*; Pine, Red (Norway) - *Pinus resinosa*; Pine, Shortleaf - *Pinus echinata*; Pine, Virginia Scrub - *Pinus virginiana*; Pine, Western Yellow (Ponderosa) - *Pinus ponderosa*; Pine, White (Eastern) - *Pinus strobus*; Plum (Prune) - *Prunus domestica*; Poplar, Balsam - *Populus balsamifera*; Poplar, Lombardy - *Populus nigra-italica*; Western Balsam (See Cottonwood, Black) *Populus trichocarpa*; Poplar, White - *Populus alba*; Privet - *Ligustrum* spp.; Redwood - *Sequoia sempervirens*; Russian Olive - *Elaeagnus angustifolia*; Spruce, Red - *Picea rubens*; Spruce, Sitka -*Picea sitchensis*; Sycamore, Mapleleaf - *Platanus acerifolia*; Sycamore, Western - *Platanus racemosa*; Tamarack (Larch) - *Larix occidentalis*; Tamarisk (See Cedar, Salt) -*Tamarix gallica*; Tree of Heaven - *Ailanthus altissima*; Walnut, Arizona - *Juglans rupestris*; Walnut, Hind's California Black - *Juglans hindsii*; Walnut, So. California Black - *Juglans californica*; Walnut, English - *Juglans regia*; Willow, Arroyo - *Salix lasiolepis*; Willow, Black -*Salix nigra*; Willow, Pussy - *Salix discolor*; Willow, Red -*Salix laevigata*; Willow, Yellow - *Salix lasiandra*.

EXAMPLE 4

Repeating the procedure of Example 1 but replacing the timothy grass pollen extract with extracts of the following grass and weed pollens yields the corresponding, respective covalently bonded BSA-allergen conjugates: Barley, Cultivated - *Hordeum vulgare*; Bluegrass, Annual-*Poa annua*; Bluegrass, Canada - *Poa compressa*; Bluegrass, Sandberg - *Poa sandbergii*; Brome Broncho-Ripgut - *Bromus rigidus*; Brome, California -*Bromus carinatus*; Brome, Cheat -*Bromus secalinus*; Brome, Soft Cheat - *Bromus mollis*; Bunch, Blue (Northwestern Bunch) - *Agropyron spicatum*; Canarygrass - *Phalaris canariensis*; Canarygrass, Reed -*Phalaris arundinacea*; Fescue, Red -*Festuca rubra*; Grama Grass, Blue (Side OOats) - *Bouteloua gracilis*; Koeler's Grass (Western Junegrass) -*Koeleria cristata*; Lovegrass, Hawaiian - *Eragrostis variabilis*; Oats, Common Cultivated -*Avena sativa*; Oatgrass, Tall -*Avena elatior (Arrhenatherum elatius)*; Quack Grass -*Agropyron repens*; Rye, Cultivated -*Secale cereale*; Ryegrass, Alkali - *Elymus triticoides*; Ryegrass, Giant Wild - *Elymus cinereus*; Ryegrass, Italian -*Lolium multiflorum*; Ryegrass, Western - *Elymus glaucus*; Salt Grass - *Distichlis stricta*; Sorghum, Common Cultivated -*Sorghum vulgare*; Sudan Grass -*Sorghum vulgare var. sudanese*; Sweet Vernal grass - *Anthoxanthum odoratum*; Velvetgrass -*Holcus ianatus*; Wheat, Cultivated - *Triticum aestivum*; Wheatgrass, Crested - *Agropyron cristatum*; Wheatgrass, Western - *Agropyron smithii*; Alfalfa - *Medicago sativa*; Aster - *Aster sinensis*; Balsam Root - *Balsamorhiza sagittata*; Bassia - *Bassia hyssopifolia*; Beach Bur -*Franseria bipinnatifida*; Burro Brush (Greasebush) - *Hymenoclea salsola*; Careless Weed - *Amaranthus palmeri*; Castor Bean - *Ricinus communis*; Cattail, Broadleaf - *Typha latifolia*; Clover, Red - *Trifolium pratense*; Clover, Sweet, Yellow - *Melilotus officinalis*; Clover, White (Dutch) - *Trifolium repens* (album); Cocklebur, Common -*Xanthium strumarium*; Cocklebur, Spiny - *Xanthium spinosum*; Cosmos - *Cosmos bipinnatus*; Daffodil -*Narcissus pseudo-narcissus*; Dahlia - *Dahlia pinnata x coccinea*; Daisy/-Chrysanthemum (Oxeyed Diasy) - *Chrysanthemum leucanthemum*; Dock, Bitter - *Rumex obtusifolius*; Dog Fennel (Mayweed) -*Anthemix cotula*; Fireweed, Alaska - *Epilobium angustifolium*; Gladiolus - *Gladiolus xhortulanus*; Greasewood - *Sarcobatus vermiculatus*; Hemp - *Cannabis sativa*; Hops - *Humulus lupulus*; Hopsage - *Grayia spinosa*; Iodine Bush (Burro Weed) - *Allenrolfea occidentalis*; Kochia (Mex. Firebush) -*Kochia scoparia*; Lily, Easter - *Lilium longiflorum*; Marigold - *Tagetes patula*; Marshelder, Burweed (Giant Poverty) - *Iva Xanthifolia*; Marshelder, Narrowleaf (August) - *Iva angustifolia*; Marshelder, True (Rough) -*Iva ciliata*; Mexican Tea -*Chenopodium ambrosioides*; Mustard, Black - *Brassica nigra*; Mustard, Common Yellow -*Brassica campestris*; Nettle - *Urtica dioica* ((*gracilis*)); Pickleweed - *Salicornia ambigua*; Pigweed, Spiny - *Amaranthus spinousus*; Poppy, California - *Eschoscholzia californica*; Povertyweed, Small - *Iva axillaris*; Rabbit Brush - *Chrysothamnus nauseosus*; Rabbit Bush (Bur Ragweed) - *Franseria deltoides*; Ragweed, Canyon - *Franseria ambrosioides*; Ragweed, Desert - *Franseria dumosa*; Ragweed, Giant - *Ambrosia trifida*; Ragweed, Silver - *Dicoria canescens*; Ragweed, Slender - *Franseria tenuifolia*; Ragweed, Southern -*Ambrosia bidentata*; Rose - *Rosa multiflora*; Sagebrush - Annual - *Artemisia annua*; Sagebrush, Coast - *Artemisia californica*; Sagebrush, Green (Tarragon)-*Artemisia dracunculus*; Sagebrush, Mugwort - *Arthemisia vulgaris heterophylla*; Sagebrush, Pasture (Carpet) - *Artemisi frigida*; Sagebrush, Sand Dune - *Artemisia pycnocephala*; Sagebrush, White (Prairie) - *Artemisia iudoviciana*; Saltbush, Annual - *Atriplex wrightii*; Scale, All - *Atriplex polycarpa*; Scale, Bract - *Artriplex serenana bracteosa*; Scale, Brewers - *Atriplex lentiformis breweri*; Scale, Lens -*Atriplex lentiformis*; Scale, Red - *Atriplex rosea*; Scale, silver (Fogweed) - *Atriplex argentea expansa*; scale, Spear - *Atriplex patula hastata*; Scale, wing (Shad) - *Atriplex canescen*; Scotch Broom - *Cytisus scoparius*; Sea Blite, California - *Suaeda californica*; Sedge - *Carex barbara*; Sheep Fat - *Atriplex confertifolia*; Snapdragon - *Antirrhinum majus*; Suaeda (See Sea Blite); Sugar Beet - *Beta vulgaris*; Sunflower - *Helianthus annuus*; Waterhemp, Western - *Acnida tamariscina*; Winter Fat - Eurotia lanata; wormseed (Jerusalem Oak) - *Chenopodium botrys*; Wormwood, Absinthe - *Artemisia absinthium*.

EXAMPLE 5

Repeating the procedure of Example 1 but replacing the timothy grass pollen extract with extracts of the following epidermals and glandular extracts yields the corresponding covalently bonded BSA-allergen conjugates: Camel Hair & Dander; Deer Hair & Dander; Feathers, Parakeet; Feathers, Pigeon; Feathers, Turkey; Fox Fur; Gerbil Hair & Epithelium; Glue, Fish; Goat Hair & Dander; Hamster Hair & Epithelium; Hog Hair & Dander; Human Hair; Mink Fur; Mohair; Monkey Hair & Epithelium; Mouse Hair & Epithelium; Poodle Hair & dander; Pyrethrum; Rabbit Hair & Epithelium; Rat Hair & Epothelium; Seal Fur; Wool, Sheep.

EXAMPLE 6

Repeating the procedure of Example 1 but replacing the timothy grass pollen extract with extracts of the following dusts yields the corresponding respective covalently bonded BSA-allergen conjugates: Acacia Gum; Alfalfa Hay; Algae, Chlorella spp.; Carragheen Gum; Coconut Fiber; Cotton Linters; Cottonseed; Dust, Barley; Dust, Corn; Dust, Grain Mill; Dust, Mattress; Dust, Oat; Dust, Pea; Dust; Rye; Dust, Soybean; Dust, Upholstery; Dust, Wheat; Dust, Wood - Cedar/-Juniper; Dust, Wood - fir/Hemlock; Dust, Wood - Gum; Dust, Wood - Mahogany; Dust, Wood - Maple; Dust, Wood - Oak Mix; Dust, Wood - Pine Mix; Dust, Wood - Redwood; Dust, Wood - Spruce; Dust, Wood - Walnut; Fern Spores, sp.; Flax Fiber; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; Tobacco, Leaf.

EXAMPLE 7

Repeating the procedure of Example 1 but replacing the timothy grass pollen extract with extracts of the following foods yields the corresponding respective covalently bonded BSA-allergen conjugates: Allspice; Almond; Apricot Food; Arrowroot; Artichoke; Asparagus; Avocado; Banana; Bay Leaf; Bean, Kidney; Bean, Lima; Bean, Navy; Bean, Pinto-Frijole; Bean, String-/Wax; Beet; Black - Eyed Pea; Blueberry; Brazil Nut; Buckwheat; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Crab; Cucumber; Curry Powder; Date; Dill;

Egg White; Egg, Yolk; Eggplant; Endive; Garlic; Gelatine; Ginger; Raisin Mix; Grapefruit; Haddock; Halibut; Hazelnut (Filbert); Herring; Honey; Hops Food; Horseradish; Lamb; Lemon; Lentil; Lime; Liver, Beef (Calves); Lobster; Mackerel; Malt; Mangoes; Maple, Syrup/Sugar; Melon, (see Muskmelon Mix); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Oregano; Oyster Mix; Papaya; Papriks; Parsley; Parsnip; Pea; Peach Food; Pear Food; Pecan Food; Pepper, Black/-White; Pepper, Bell (Green/Red); Perch, Lake; Pineapple; Plum/-Prune Mix; Poppy Seed; Pumkin; Rabbit Meat; Radish; Raspberry; Snapper; Rhubarb; Rice, Wild; Rye, Whole (Grain); Safflower Seed; Sage; Salmon; Scallops; Sesame Seed; Sole; Spinach; Squash, Mix; Strawberry; Sugar (Beet); Sugar (Cane); Sunflower Seeds; Tapioca; Tea; Thyme; Trout; Turkey; Turnip; Vanilla; Walnut Food, Black; Walnut Rood, English; Watermelon; Whitefish; Yeast, Brewers; Yeast Mix (Bakers/Brewers, *Sacchoromyces cereisiae*).

EXAMPLE 8

Repeating the procedure of Example 1 but replacing the timothy grass pollen extract with extracts of the following molds yields the corresponding respective covalently bonded BSA-allergen conjugates: *Aspergillus clavatus; Aspergillus glaucus; Aspergillus nidulans; Aspergillus niger; Aspergillus restrictus; Aspergillus sydowi; Aspergillus terreus; Botrytis cinerea; Cephalosporium acremonium; Cephalothecium (Trichothecium) reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum (Cladosporium); Monilia sitophila;* Mycogone sp.; *Neurospora crassa; Nigrospora sphaerica;* Oidiodendrum sp.; *Paecilomyces varioti; Penicillium artramentosum; Penicillium biforme; Penicillium carminoviolaceum; Penicillium chrysogenum; Penicillium digitatum; Penicillium expansum; Pencillium glaucum; Penicillium intricatum; Penicillium luteum; Penicillium roqueforti; Penicillium roseum; Phoma herbarum; Pleospora sp.; Poria sp.; Pullularia pullulans; Rhizopus nigricans; Rhodotorula glutinis; Saccharomyces cerevisiae* (See Yeast Mix); *Scopulariopsis brevicaulis;* Spondylocladium sp.; *Sporobolomyces salmonicolor; Stemphylium botryosum; Streptomyces griseus; Trichoderma viride; Typhula idahoensis; Verticillum alboatrum.*

EXAMPLE 9

Repeating the procedure of Example 1 but replacing the timothy grass pollen extract with extracts of the following smuts yields the corresponding respective covalently bonded BSA-allergen conjugates: Smut, Barley; Smut, Bermuda; Smut Corn; Smut, Johnson; Smut, Oat; Smut, Sorghum; Smut, Wheat.

EXAMPLE 10

Repeating the procedure of Example 1 but replacing the timothy grass pollen extract with extracts of the following insects and insect venoms yields the corresponding covalently bonded BSA-allergen conjugates: Ants, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea antigen; Fruit Flies; Gnat sp.; Horney, Black and Yellow; Horse Fly; House Fly; Mayfly sp.; Mite (*D. farinae*); Mosquito Mix; Moth, Miller; Wasp; Yellow Jacket; Honey Bee Venom Protein -*Apis mellifera*; Wasp Venom Protein - Polistes sp.; White-faced Horner Venom Protein - *Dolichovespula maculata*; Yellow Hornet Venom Protein - *Dolichovespula arenaria*; Yellow Jacket Venom Protein - Vespula sp.; Mixed Vespid Venom Protein.

EXAMPLE 11

To a solution of timothy grass pollen allergen extract (3 mg/ml) was added 10 microliters of a 5 wt/% bovine serum serum (BSA) solution. After addition, the solution was kept at 4° C. and added with 10 microliters of a 1.0 wt/% solution of glutaraldehyde in PBS solution (0.01 M phosphate, 0.1% sodium azide, deionized water, pH 8.5). The mixture was gently stirred at 4° C. for 20 minutes. The additions of both BSA and glutaraldehyde were repeated three more times. The final mixture was allowed to stand at 4° C. overnight to yield a covalently bonded conjugate with timothy grass pollen allergen.

EXAMPLE 12

Repeating the procedure of Example 11 but replacing the timothy grass pollen allergen with allergen extracts listed in Example 2 yields the corresponding covalently bonded BSA-allergen conjugates.

EXAMPLE 13

Repeating the procedure of Example 11 but replacing the timothy grass pollen allergens with allergen extracts listed in Example 3 yields the corresponding covalently bonded BSA-allergen pollen grass conjugates.

EXAMPLES 14

Repeating the procedure of Exampel 11 but replacing the timothy grass pollen allergens with allergen extracts listed in Example 4 yields the corresponding covalently bonded conjugates of BSA with grass and weed pollen allergens.

EXAMPLE 15

Repeating the procedure of Example 11 but replacing the timothy grass pollen allergens with allergens extracts listed in Example 5 yields the corresponding covalently bonded conjugates of BSA with epidermals and glandular extract allergens.

EXAMPLE 16

Repeating the procedure of Example 11 but replacing the timothy grass pollen allergens with allergen extracts listed in Example 6 yields the corresponding covalently bonded BSA-dust allergen conjugates.

EXAMPLE 17

Repeating the procedure of Example 11 but replacing the timothy grass pollen allergens with allergen extracts listed in Example 7 yields the corresponding covalently bonded BSA-food allergen conjugates.

EXAMPLES 18

Repeating the procedure of Example 11 but replacing the timothy grass pollen allergens with allergen extracts listed in Example 8 yields the corresponding covalently bonded BSA-mold allergen conjugates.

EXAMPLE 19

Repeating the procedure of Example 11 but replacing the timothy grass pollen allergens with allergen extracts listed in Example 9 yields the corresponding covalently bonded BSA-smut allergen conjugates.

EXAMPLES 20

Repeating the procedure of Example 11 but replacing the timothy grass pollen allergens with allergen extracts listed in Example 10 yields the corresponding covalently bonded conjugate of BSA with insect and insect venom allergens.

EXAMPLE 21

The timothy grass pollen allergens-conjugate with BSA prepared in Example 1 was diluted in phosphate buffer, pH 8.5. To each microtiter well was added precisely 100 microliters of the diluted conjugate solution. The coating process was allowed to proceed at room temperature for 2 hours (or overnight). At the end of the coating process, the liquid in each well was removed by aspiration.

The wells were washed three times (3×200 microliters) with a phosphate washing buffer containing sorbitol and TRITON X405 The wells thus coated can be used for assaying patient serum for timothy grass pollen allergen specific IgE antibodies.

EXAMPLES 22

The procedure of Example 21 was repeated but replacing the timothy grass pollen extract - BSA conjugate with the BSA conjugate products of Example 2. This yielded microtiter wells each having adhered thereto a BSA-allergen extract conjugate of: *Grasses* - Bermuda Grass, *Cynodon dactylon*, Orchard Grass, *Dactylis glomerata*, Perennial Rye Grass, *Lolium perenne*, June Grass (Kentucky Blue), *Poa pratensis*, Bent Grass, *Agrostis maritima*, Johnson Grass, *Sorghum halepense*, Brome Grass, *Bromus inermis*, Bahia Grass, *Paspalum notatum*, Corn Grass, *Zea mays, Meadow Fescue, Festuca elatior*, and Redtop, *Agrostis alba; Weeds* - Short Ragweed, *Ambrosia artemisifolia*, Western Ragweed, *Ambrosia Psilostachya*, False Ragweed, *Franseria acanthicarpa*, Sagebrush (common), *Arteisia tridentata*, Dandelion, *Taraxacum vulgare*, English Plantain, *Plantago lanceolata*, Lamb's Quarters, *Chenopodium album*, Russian Thistle, *Salsola kali*, Goldenrod, Solidago sp., Pigweed, *Amaranthus retroflexus*, Dock (yellow), *Rumex crispus*, and Sheep Sorrel, *Rumex acetosella; Trees* - Box Elder (Maple), *Acer negundo*, Alder, *Alnus rhombifolia*, Birch, *Betula nigra*, Mountain Cedar, *Juniperus sabinoides*, White Oak, *Quercus alba*, Elm, *Ulmus americana*, Olive, *Olea europaea*, Black Walnut, *Juglans nigra*, Sycamore, *Platanus occidentalis*, Cottonwood, *Populus trichocarpa*, White Ash, *Fraxinus americana*, White Pine, *Pinus monticola*, Eucalyptus, Eucalyptus sp., Acacia, *Acacia baileyana*, Aspen, *Populus tremuloides*, Arizona Cypress, *Cupressus arizonica*, Mesquite, *Prosopis juliflora*, Privet, *Ligustrum ovalifolium*, Melaleuca (Punk Tree), *Melaleuca leucadendron*, and Australian Pine (Beefwood), *Casuarina equisetifolia*; Epidermals - Cat Epithelium, Dog Hair and Dander, Horse Hair and Dander, Cow Hair and Dander, Guinea Pig Hair and Dander, Feather Mix (Chicken, Duck & Goose), and Wool (Sheep); Molds - *Penicillium notatum, Cladosporium herbarum, Aspergillus fumigatus, Mucor racemosus, Candida albicans*, and *Alternaria tenuis; House Dust; Mite* - *Dermatophagoides farinae*; and *Foods* - Milk, Wheat, Corn, Rice, Peanut, Soybean, Shrimp, Tomato, Pork, Carrot, Orange, Potatoe, Tuna, Beef, Lamb, Chicken, Whole Egg, Yeast (Bakers), Sweet Potato, Cabbage, Lettuce, Pepper (Bell), Apple, Cranberry, Grape, Barley, and Onion.

EXAMPLE 23

Repeating the procedure of Example 21 but replacing the timothy grass pollen extract - BSA conjugate with the BSA conjugate products of Example 3 yields microtiter wells each having adhered thereto a BSA-allergen extract conjugate of: Acacia -*Acacia longifolia*; Ailanthus (See Tree of Heaven) - *Ailanthus altissima*; Alder, Mountain (Tag) (Slender) - *ainus tenuifolia/incana*; Alder, Red (Oregon) -*Alnus rubra*; Alder, Sitka - *Alnus sinuata*; Almond - *Prumus amygdalus*; Apple - *Pyrus malus* (*Malus pumila*); Apricot - *Prunus armeniaca*; Arbor Vitae, Oriental (Ornamental) - *Betula papyrifera*; Birch, Spring - *Betula fontinalis*; Birch, White (Weeping) - *Betula pendula*; Birch, Yellow - *Betula lutea*; Blue Beech (Am. Hornbeam) -*Carpinus carolineana*; Bottle Brush - *Callistemon citrinus*; Butternut - *Juglans cinerea*; Carob Tree - *Ceratonia siliqua*; Cedar, Deodar - *Cedrus deodora*; Cedar, Giant -*Thuja plicata*; Cedar, Incense - *Linocedrus decurrens*; Cedar, Japanese - *Cryptomeria japonica*; Cedar, Port Orford (Lawson Cypress) - *Chamaecyparis lawsoniana*; Cedar, Red -*Juniperus virginiana*; Cedar, Rocky Mountain - *Juniperus scopulorum*; Cedar, Salt (Tamarisk) - *Tamarix gallica*; Cedar, White - *Thuja occidentalis*; Cherry, *Prunus cerasus*; Chestnut, American - *Castanea dentata*; Chestnut, Horse -*Aesculus hippocastanum*; Cottonwood, Common - *Populus deltoides*; Cottonwood, Fremont - *Populus fremontii*; Cypress, Bald (White) - *Taxodium distichum*; Cypress, Italian - *Cupressus sempervirens*; Cypress, Monterey -*Cupressus macrocarpa*; Elderberry - *Sambucus glauca*; Elm, Cedar (Fall Blooming) - *Ulmus crassifolia*; Elm, Chinese -*Ulmus parvifolia*; Elm, Siberian - *Ulmus pumila*; Elm, Slippery - *Ulmus fulva* (rubra); Fir, Douglas - *Pseudotsuga menziesii*; Fir, Red (Noble) - *Abies nobilis* (procera); Fir, White - *Abies concolor*; Gum, Sweet - *Liquidambar styraciflua*; Hackberry - *Celtis occidentalis*; Hazelnut, American - *Corylus americana*; Hemlock, Eastern - *Tsuga canadensis*; Hemlock, Western - *Tsuga heterophylla*; Hickory, Shagbark - *Carya ovata*; Hickory, Shellbark -*Carya laciniosa*; Hickory, White - *Carya tomentosa*; Ironwood (Hop-Hornbeam) - *Ostrya virginiana*; Juniper, California - *Juniperus californica*; Juniper, Chinese -*Juniperus chinensis*; Juniper, Oneseed - *Juniperus monosperma*; Juniper, Pinchot - *Juniperus pinchotti*; Juniper, Utah -Juniperus osteosperma (juniperus utahensis); Juniper, Western - *Juniperus occidentalis*; Lilac - *Syringa vulgaris*; Linden (Basswood) - *Tilia americana*; Locust, Black - *Robinia pseudocacia*; Maple, Big-Leaf (Coast) - *Acer macrophyllum*; Maple, Hard (Sugar) - *Acer saccharum*; Maple, Red - *Acer rubrum*; Maple, Soft (Silver) - *Acer saccharinum*; Mock Orange, Wild (Syringa) - *Philadelphus lewsii*; Mulberry, Paper - *Broussonetia papyifera*; Mulberry, Red - *Morus rubra*; Mulberry, White - *Morus alba*; Oak, Arizona (Gambel) - *Quercus gambelii*; Oak, Arizona Scrub (Canyon) - *Quercus chrysolepsis*; Oak, Black (Yellow) -*Quercus velutina*; Oak, Black Jack - *Quercus marilandica*; Oak, Bur - *Quercus macrocarpa*; Oak, California Black -*Quercus kelloggii-californica*; Oak, California Scrub - *Quercus dumosa*; Oak, Coast Live - *Quercus agrifolia*; Oak, Engelmann - *Quercus engelmanii*; Oak, Garry (Western White) -*Quercus garryana*; Oak, Holly - *Quercus ilex*; Oak, Interior Live - *Quercus wislizenii*; Oak, Post - *Quercus stellata*; Oak, Red - *Quercus rubra*; Oak, Swamp (Pin) - *Quercus palustris*; Oak, Valley - *Quercus lobata*; Oak, Virginia Live - *Quercus virginiana*; Oak, Water - *Quercus nigra*; Olive - *Olea europaea*; Orange - *Citrus sinensis*; Osage Orange - *Maclura pomifera*; Palm, Date - *Phoenix dactylifera*; Palm, Dwarf - *Chamaerops humulis*; Palm, Canary Island Date (Ornamental) - *Phoenix canariensis*; Palm, Queen - *Cocos plumosa*; Peach - *Prunus persica*; Pear - *Pyrus communis*; Pecan - *Carya pecan*; Pepper Tree, California - *Schinus molle*; Pepper Tree, Brazilian - *Schinus terebinthifolius*; Pine, Austrian - *Pinus nigra*; Pine, Canary Island - *Pinus canariensis*; Pine, Digger - *Pinus sabiniana*; Pine, Loblolly - *Pinus taeda*; Pine, Lodgepole - *Pinus contorta*; Pine, Monterey - *Pinus radiata*; Pine, Pinyon - *Pinus edulis*; Pine, Red (Norway) - *Pinus resinosa*; Pine, Shortleaf - *Pinus echinata*; Pine, Virginia Scrub - *Pinus virginiana*; Pine, Western Yellow (Ponderosa) - *Pinus ponderosa*; Pine, White (Eastern) - *Pinus strobus*; Plum (Prune) - *Prunus domestica*; Poplar, Balsam - *Populus balsamifera*; Poplar, Lombardy - *Populus nigra-italica*; Western Balsam (See Cottonwood, Black) *Populus trichocarpa*; Poplar, White - *Populus alba*; Privet - Ligustrum spp.; Redwood - *Sequoia sempervirens*; Russian Olive - *Elaeagnus angustifolia*; Spruce, Red, - *Picea rubens*; Spruce, Sitka -*Picea sitchensis*; Sycamore, Mapleleaf - *Platanus acerifolia*; Sycamore, Western - *Platanus racemosa*; Tamarack (Larch) - *Larix occidentalis*; Tamarisk (See Cedar, Salt) -*Tamarix gallica*; Tree of Heaven - *Ailanthus altissima*; Walnut, Arizona - *Juglans ruestris*; Walnut, Hind's California Black - *Juglans hindsii*; Walnut, So. California Black - *Juglans californica*; Walnut, English - *Juglans regia*; Willow, Arroyo - *Saliz lasiolepis*; Willow, Black -*Salix nigra*; Willow, Pussy - *Salix discolor*; Willow, Red - *Salix laevigata*; Willow, Yellow - *Salix lasiandra*.

EXAMPLE 24

Repeating the procedure of Example 21 but replacing the timothy grass pollen extract - BSA conjugate with the BSA conjugate products of Example 4 yields microtiter wells each having adhered thereto a BSA-allergen extract conjugate of Barley, Cultivated - *Hordeum vulgare*; Bluegrass, Annual -*Poa annua*; Bluegrass, Canada - *Poa compressa*; Bluegrass, Sandberg - *Poa sandbergii*; Brome Broncho-Ripgut - *Bromus rigidus*; Brome, California -*Bromus carinatus*; Brome, Cheat -*Bromus secalinus*; Brome, Soft Cheat - *Bromus mollis*; Bunch, Blue (Northwestern Bunch) - *Agropyron spicatum*; Canarygrass - *Phalaris canariensis*; Canarygrass, Reed -*Phalaris arundinacea*; Fescue, Red -*Festuca rubra*; Grama Grass, Blue (Side Oats) - *Bouteloua gracilis*; Koeler's Grass (Western Junegrass) -*Koeleria cristata*; Lovegrass, Hawaiian - *Eragrostis variabilis*; Oats, Common Cultivated -*Avena sativa*; Oatgrass, Tall -*Avena elatior (Arrhenatherum elatius)*; Quack Grass -*Agropyron repens*; Rye, Cultivated -*Secale cereale*; Ryegrass, Alkali - *Elymus triticoides*; Ryegrass, Giant Wild - *Elymus cinereus*; Ryegrass, Italian -*Lolium multiflorum*; Ryegrass, Western - *Elymus glaucus*; Salt Grass - *Distichlis stricta*; Sorghum, Common Cultivated -*Sorghum vulgare*; Sudan Grass -*Sorghum vulgare var. sudanese*; Sweet Vernal grass - *Anthoxanthum odoratum*; Velvetgrass -*Holcus ianatus*; Wheat, Cultivated - *Triticum aestivum*; Wheatgrass, Crested - *Agropyron cristatum*; Wheatgrass, Western - *Agropyron smithii*; Alfalfa - *Medicago sativa*; Aster - *Aster sinensis*; Balsam Root - *Balsamorhiza sagittata*; Bassia - *Bassia hyssopifolia*; Beach Bur -*Franseria bipinnatifida*; Burro Brush (Greasebush) - *Hymenoclea salsola*; Careless Weed - *Amaranthus palmeri*; Castor Bean - *Ricinus communis*; Cattail, Broadleaf - *Typha latifolia*; Clover, Red - *Trifolium pratense*; Clover, Sweet, Yellow - *Melilotus officinalis*; Clover, White (Dutch) - *Trifolium repens* (album); Cocklebur, Common -*Xanthium strumarium*; Cocklebur, Spiny - *Xanthium spinosum*; Cosmos - *Cosmos bipinnatus*; Daffodil - *Narcissus pseudonarcissus*; Dahlia - *Dahlia pinnata x coccinea*; Daisy/Chrysanthemum (Oxeyed Daisy) - *Chrysanthemum leucanthemum*; Dock, Bitter - *Rumex obtusifolius*; Dog Fennel (Mayweed) -*Anthemix cotula*; Fireweed, Alaska - *Epilobium angustifolium*; Gladiolus - *Gladiolus Xhortulanus*; Greasewood - *Sarcobatus vermiculatus*; Hemp - *Cannabis sativa*; Hops - *Humulus lupulus*; Hopsage - *Grayia spinosa*; Iodine Bush (Burro Weed) - *Allenrolfea occidentalis*; Kochia (Mex. Firebush) -*Kochia scoparia*; Lily, Easter - *Lilium longiflorum*; Marigold - *Tagetes patula*; Marshelder, Burweed (Giant Poverty) - *Iva xanthifolia*; Marshelder, Narrowleaf (August) - *Iva angustifolia*; Marshelder, True (Rough) -*Iva ciliata*; Mexican Tea -*Chenopodium ambrosioides*; Mustard, Black - *Brassica nigra*; Mustard, Common Yellow -*Brassica campestris*; Nettle - *Urtica dioica* (gracilis); Pickleweed - *Salicornia ambigua*; Pigweed, Spiny - *Amaranthus spinosus*; Poppy, California - *Eschoscholzia californica*; Povertyweed, Small - *Iva axillaris*; Rabbit Brush - *Chrysothamnus nauseosus*; Rabbit Bush (Bur Ragweed) - *Franseria deltoides*; Ragweed, Canyon - *Franseria ambrosioides*; Ragweed, Desert - *Franseria dumosa*; Ragweed, Giant - *Ambrosia trifida*; Ragweed, Silver - *Dicoria canescens*; Ragweed, Slender - *Franseria tenuifolia*; Ragweed, Southern -*Ambrosia bidentata*; Rose - *Rosa multiflora*; Sagebrush - Annual - *Artemisia annua*; Sagebrush, Coast - *Artemisia californica*; Sagebrush, Green (Tarragon) -*Arthemisia dracunculus*; Sagebrush, Mugwort - *Arthemisia vulgaris heterophylla*; Sagebrush, Pasture (Carpet) - *Arthemisi frigida*; Sagebrush, Sand Dune - *Artemisia pycnocephala*; Sagebrush, White (Prairie) - *Artemisia Iudoviciana*; Saltbush, Annual - *Atriplex wrightii*; Scale, All - *Atriplex polycarpa*; Scale, Bract - *Atriplex serenana bracteosa*; Scale, Brewers - *Atriplex lentiformis breweri*; Scale, Lens -*Atriplex lentiformis*; Scale, Red - *Atriplex rosea*; Scale, Silver (Fogweed) - *Atriplex argentea expansa*; Scale, Spear - *Atriplex patula hastata*; Scale, Wing (Shad) -*Atriplex canescen*; Scotch Broom - *Cytisus scoparius*; Sea Blite, California - *Suaeda californica*; Sedge - *Carex barbara*; Sheep Fat - *Atriplex confertifolia*; Snapdragon - *Antirrhinum majus*; Suaeda (See Sea Blite); Sugar Beet - *Beta vulgaris*; Sunflower - *Helianthis annuus*; Waterhemp, Western - *Acnida tamariscina*; Winter Fat - *Eurotia lanata*; Wormseed (Jerusalem Oak) - *Chenopodium botrys*; Wormwood, Absinthe - *Athemisia absinthium*.

EXAMPLE 25

Repeating the procedure of Example 21 but replacing the timothy grass pollen extract - BSA conjugate with the BSA conjugate products of Example 5 yields microtiter wells each having adhered thereto a BSA-allergen extract conjugate of Camel Hair & Dander; Deer Hair & Dander; Feathers, Parakeet; Feathers, Pigeon; Feathers, Turkey; Fox Fur; Gerbil Hair & Epithelium; Glue, Fish; Goat Hair & Dander; Hamster Hair & Epithelium; Hog Hair & Dander; Human Hair; Mink Fur; Mohair; Monkey Hair & Epithelium; Mouse Hair & Epithelium;

Poodle Hair & Dander; Pyrethrum; Rabbit Hair & Epithelium; Rat Hair & Epithelium; Seal Fur; Wool, Sheep.

EXAMPLE 26

Repeating the procedure of Example 21 but replacing the timothy grass pollen extract - BSA conjugate with the BSA conjugate products of Example 6 yields microtiter wells each having adhered thereto a BSA-allergen extract conjugate of Acacia Gum; Alfalfa Hay; Algae, Chlorella spp.; Carragheen Gum; Coconut Fiber; Cotton Linters; Cottonseed; Dust, Barley; Dust, Corn; Dust, Grain Mill; Dust, Mattress; Dust, Oat; Dust, Pea; Dust, Rye; Dust, Soybean; Dust, Upholstery; Dust, Wheat; Dust, Wood - Cedar/Juniper; Dust, Wood - fir/Hemlock; Dust, Wood - Gum; Dust, Wood - Mahogany; Dust, Wood - Maple; Dust, Wood - Oak Mix; Dust, Wood - Pine Mix; Dust, Wood - Redwood; Dust, Wood - Spruce; Dust, Wood - Walnut; Fern Spores, sp.; Flax Fiber; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; or Tobacco, Leaf.

EXAMPLE 27

Repeating the procedure of Example 21 but replacing the timothy grass pollen extract - BSA conjugate with the BSA conjugate products of Example 7 yields microtiter wells each having adhered thereto a BSA-allergen extract conjugate of Allspice; Almond; Apricot Food; Arrowroot; Artichoke; Asparagus; Avocado; Banana; Bay Leaf; Bean, Kidney; Bean, Lima; Bean, Navy; Bean, Pinto-Frijole; Bean, String/Wax; Beet; Black-Eyed Pea; Blueberry; Brazil Nut; Buckwheat; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Crab; Cucumber; Curry Powder; Date; Dill; Egg White; Egg, Yolk; Eggplant; Endive; Garlic; Gelatine; Ginger; Raisin Mix; Grapefruit; Haddock; Halibut; Hazelnut (Filbert); Herring; Honey; Hops Food; Horseradish; Lamb; Lemon; Lentil; Lime; Liver, Beef (Calves); Lobster; Mackerel; Malt; Mangoes; Maple, Syrup/Sugar; Melon, (see Muskmelon Mix); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Oregano; Oyster Mix; Papaya; Paprika; Parsley; Parsnip; Pea; Peach Food; Pear Food; Pecan Food; Pepper, Black/White; Pepper, Bell (Green/Red); Perch, Lake; Pineapple; Plum/Prune Mix; Poppy Seed; Pumpkin; Rabbit Meat; Radish; Raspberry; Snapper; Rhubarb; Rice, Wild; Rye, Whole (Grain); Safflower Seed; Sage; Salmon; Scallops; Sesame Seed; Sole; Spinach; Squash, Mix; Strawberry; Sugar (Beet); Sugar (Cane); Sunflower Seeds; Tapioca; Tea; Thyme; Trout; Turkey; Turnip; Vanilla; Walnut Food, Black; Walnut Food, English; Watermelon; Whitefish; Yeast, Brewers; Yeast Mix (Bakers/Brewers, *Sacchoromyces cervisiae*).

EXAMPLE 28

Repeating the procedure of Example 21 but replacing the timothy grass pollen extract - BSA conjugate with the BSA conjugate products of Example 8 yields microtiter wells each having adhered thereto a BSA-allergen extract conjugate of *Aspergillus clavatus; Aspergillus glaucus; Aspergillus nidulans; Aspergillus niger; Aspergillus restrictus; Aspergillus sydowi; Aspergillus terreus; Botrytis cinerea; Cephalosporium acremonium; Cephalothecium (Trichothecium) reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis*; Helminthosporium; Hormodendrum (Cladosporium); *Monilia sitophila*; Mycogone sp.; *Neurospora crassa; Nigrospora sphaerica*; Oidiodendrum sp.; *Paecilomyces varioti; Pencillium artramentosum; Pencillium biforme; Pencillium carminoviolaceum; Pencillium chrysogenum; Penicillium digitatum; Penicillium expansum; Penicillium glaucum; Penicillium intricatum; Penicillium luteum; Penicillium roqueforti; Pencillium roseum; Phoma herbarum*; Pleospora sp.; Poris sp.; *Pullularia pullulans; Rhizopus nigricans; Rhodotorula glutinis: Saccharomyces cerevisiae* (See Yeast Mix); *Scopulariopsis brevicaulis*; Spondylocladium sp.; *Sporobolomyces salmonicolor; Stemphylium botryosum; Streptomyces griseus; Trichoderma viride; Typhula idahoensis; Verticillum alboatrum.*

EXAMPLE 29

Repeating the procedure of Example 21 but replacing the timothy grass pollen extract - BSA conjugate with the BSA conjugate products of Example 9 yields microtiter wells each having adhered thereto a BSA-allergen extract conjugate of Smut, Barley; Smut, Bermuda; Smut Corn; Smut, Johnson; Smut, Oat; Smut, Sorghum; or Smut, Wheat.

EXAMPLE 30

Repeating the procedure of Example 21 but replacing the timothy grass pollen extract - BSA conjugate with the BSA conjugate products of Example 10 yields microtiter wells each having adhered thereto a BSA-allergen extract conjugate of Ants, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea antigen; Fruit Flies; Gnat sp.; Horney, Black and Yellow; Horse Fly; House Fly; Mayfly sp.; Mite (*D. farinae*); Mosquito Mix; Moth, Miller; Wasp; Yellow Jacket; Honey Bee Venom Protein - *Apis mellifera*; Wasp Venom Protein - Polistes sp.; White-faced Horner Venom Protein - *Dolichovespula maculata; Yellow Hornet Venom Protein - Dolichovespula arenaria*; Yellow Jacket Venom Protein - *Vespula sp.*; or Mixed Vespid Venom Protein.

EXAMPLE 31

Repeating the procedure of Example 21 but replacing the timothy grass pollen extract - BSA conjugate product of Example 1 with the glutaraldehyde derived timothy grass pollen extract - BSA conjugate of Example 11 yields a microtiter well to which the conjugate is adhered.

Example 32

Repeating the procedure of Example 21 but replacing the timothy grass pollen extract - BSA conjugate product of Example 1 with the glutaraldehyde derived allergenic extract - BSA conjugates of Examples 12 through 19 inclusive yields microtiter wells to each of which is adhered a corresponding respective BSA allergen conjugate of a tree pollen, grass or weed pollen, epidermal or glandular extract, dust, food, mold, smut, insect or insect venom.

EXAMPLE 33

A microtiter plate well product of Example 21 to which a BSA conjugate of timothy grass pollen allergen is adhered is contacted with patient serum containing timothy grass pollen allergen specific IgE and incubated for 2 hrs. The serum is removed, and the well washed three times with a buffered rinse solution containing 0.85 wt. % sodium chloride, 0.05 wt. % TRITON X405 and 0.1 wt. % sodium azide preservative in a 0.01 aqueous phosphate buffer solution, pH 7.2. Serum IgE specific antibody for timothy grass pollen allergen is conjugated to the microtiter plate well surface.

The microtiter plate well is then contacted with 100 microliters of a solution of alkaline phosphatase conjugated anti-human IgE monoclonal antibody prepared according to a modified procedure of M. O'Sullivan, et al, *Anilytical Biochem.*, Vol. 100, page 100(1979). The monoclonal antibody is applied in a solution of 0.01 M phosphate buffered saline, pH 7.2, containing 4 wt. % polyethylene glycol having a molecular weight of 4000 (PEG 4000), 0.05 wt. % TRITON X-405, and 0.1 wt. % sodium azide preservative. The alkaline phosphatase conjugated anti-human IgE monoclonal antibody solution is removed from the microtiter plate well, and it is rinsed three times with the buffered rinse solution described above.

To the microtiter plate well is then added 100 microliters of a substrate solution containing $10^{-4}$ M 4-methyl umbelliferyl phosphate in 1.25 M 2-amino-2-methyl-propanol, pH 9.5 in deionized water containing 0.125 mM magnesium chloride and 0.1 wt. % sodium azide. After 60 minutes, the fluorescence level is read with a fluorometer with the excitation at 365 nm and the reading at 450 nm. By comparing the reading with levels measured by repeating the procedure with control solutions having konwn concentrations of serum specific IgE for timothy pollen allergen, the derum specific IgE level in the patient serum is determined.

EXAMPLE 34

The procedure of Example 33 is repeated replacing the microtiter plate well with the timothy grass pollen extract adhered thereto with the adherent microtiter plate well products of Example 22 through 32, inclusive, having other allergens adhering thereto to determine the allergen specific IgE levels in the patient serum specific to the respective allergens.

EXAMPLE 35

A microtiter plate well product of Example 21 (to which a BSA conjugate of timothy grass pollen allergen is adhered) is rinsed for 5 minutes with a buffered rinse solution containing 0.85 wt. % sodium chloride, 0.05 wt. % TRITON X405, 0.01 wt. % BSA, and 0.1 wt. % sodium azide preservative in a 0.01 aequous phosphate buffer solution, pH 7.2, and the surplus is removed. The prerinsed microtiter plate is then contacted with patient serum containing timothy grass pollen allergen specific IgE and incubated for 2 hrs. The serum is removed, and the well washed three times with the buffered rinse solution.

The buffered rinse solution is prepared by diluting the following concentrate with 50 parts by volume distilled or deionized water to one part by volume concentrate:

| Bovine serum albumin | 0.5 wt. % |
|---|---|
| Non-ionic surfactant (TRITON X-405) | 0.1 wt. % |
| Sodium Chloride | 17 wt. % |
| Sodium azide | 2 wt. % |
| Sodium phosphate | 0.05 M |
| pH adjusted to | 7.4 |

Serum IgE specific antibody for timothy grass pollen allergen is conjugated to the microtiter plate well surface.

The microtiter plate well is then contacted with 100 microliters of a solution of alkaline phosphatase conjugated anti-human IgE monoclonal antibody prepared according to a modified procedure of M. O'Sullivan, et al, *Analytical Biochem.*, Vol. 100, page 100(1979). The monoclonal antibody is applied in a solution of 0.01 M phosphate buffered saline, pH 7.2, containing 4 wt. % polyethylene glycol having a molecular weight of 4000 (PEG 4000), 0.05 wt. % TRITON X-405, 0.01 wt. % BSA, and 0.1 wt. % sodium azide preservative. The alkaline phosphatase conjugated anti-human IgE monoclonal antibody solution is removed from the microtiter plate well, and it is rinsed three times with the buffered rinse solution described above.

To the microtiter plate well is then added 100 microliters of a substrate solution containing $10^{-4}$ M 4-methyl umbelliferyl phosphate in 1.25 M 2-amino-2-methyl-propanol, pH 9.5 in deionized water containing 0.125 mM magnesium chloride and 0.1 wt. % sodium azide. After 60 minutes, the fluorescence level is read with a fluorometer with the excitation at 365 nm and the reading at 450 nm. By comparing the reading with levels measured by repeating the procedure with control solutions having known concentrations of serum specific IgE for timothy pollen allergen, the serum specific IgE level in the patient serum is determined.

EXAMPLE 36

The procedure of Example 35 is repeated replacing the microtiter plate well with the timothy grass pollen extract adhered thereto with the adherent microtiter plate well products of Example 22 through 32, inclusive, having other allergens adhering thereto to determine the allergen specific IgE levels in the patient serum specific to the respective allergens.

EXAMPLE 37

In this example, allergen derived from Perennial Ryegrass is adhered to a well of a black, opaque polystyrene microtiter plate. The well is washed with methanol and dried. A 1:200 dilution of a 1:10 extract from Perennial Ryegass Pollen (a 1:10 extract contains about 100,000 allergy units by the FDA suggested standards) in phosphate buffered saline having a pH of 8.5 is prepared, and 100 microliters of extract solution is pipetted into the well. After incubation for 2 hours (or overnight) at room temperature, the excess liquid is removed, and the well is washed 3 times with a 5 to 10% aqueous solution of sucrose or sorbitol and dried.

EXAMPLE 38

Repeating the procedure of Example 37 with allergens derived from each of the tree pollens described in Example 3 provides microtiter wells to which the corresponding respective tree pollen allergen is adhered.

EXAMPLE 39

Repeating the procedure of Example 3 with allergens derived from each of the grass weed pollens described in Example 3 provides microtiter wells to which the corresponding grass or weed pollen allergen is adhered.

EXAMPLE 40

Repeating the procedure of Example 37 with allergens derived from each of the epidermals and glandular extracts described in Example 4 provides microtiter wells to which the corresponding epidermal or glandular extract allergen is adhered.

EXAMPLE 41

Repeating the procedure of Example 37 with allergens derived from each of the dusts described in Example 5 provides microtiter wells to which the corresponding dust allergen is adhered.

EXAMPLE 42

Repeating the procedure of Example 37 with allergens derived from each of the foods described in Example 6 providing microtiter wells to which the corresponding food allergen is adhered.

EXAMPLE 43

Repeating the procedure of Example 37 with allergens derived from each of the molds described in Example 7 provides microtiter wells to which the corresponding mold allergen is adhered.

EXAMPLE 44

Repeating the procedure of Example 37 with allergens derived form each of the smuts described in Example 8 provides microtiter wells to which the corresponding smut allergen is adhered.

EXAMPLE 45

Repeating the procedure of Example 37 with allergens derived from each of the insets and insect venoms described in Example 9 provides microtiter plates to which the corresponding insect or insect venom allergen is adhered.

EXAMPLE 46

The product of Example 37, a microtiter plate well to which perennial ryegrass pollen allergen is adhered, is washed 3 times with 0.9% sodium chloride rinse solution containing 0.05% Triton X-405 (Octylphenoxypolyethoxyethanol). Patient serum of a patient suffering an allergy to perennial ryegrass pollen (100 microliters) is added to the well and incubated at room temperature for 2 hr. The well is aspirated and washed 3 times with the above saline rinse solution.

Then 100 microliters of solution containing one microgram of alkaline phosphatase labeled monoclonal anti-IgE antibody in a PBS solution containing 4%(w/v) polyethylene glycol 4000 and 0.05% Tritio X-405 is added to the well and incubated for 2 hr at room temperature. The well is then aspirated and washed 3 times with the above rinse solution.

Then 100 microliters of an aqueous $10^{-4}$ M 4-methyl-umbelliferyl phosphate solution containing 1.25 M 2-amino-2-methyl-1-propanol buffer and 0.125 mM. magnesium chloride, pH 9.5, is added to the well and incubated for 60 minutes at room temperature. The fluorescence level is read with a fluorometer with excitation at 365 nm and the reading at 450 nm.

The invention claimed is:

1. A method for identifying and quantifying allergen specific IgE levels in patient serum comprising
   (a) Contacting an insoluble support having an allergen-conjugate comprised of an allergen covalenty bonded to a soluble protein or an amino acid polymer adhering thereto with patient serum for sufficient time to permit conjugation and removing the patient serum therefrom;
   (b) Contacting the insoluble support with anti-IgE antibody labeled with a fluorogenic enzyme for a time between 30 and 180 minutes and sufficient to permit conjugation and removing unconjugated anti-IgE antibody therefrom;
   (c) Contacting the insoluble support with a solution of a substrate which undergoes reaction in the presence of the fluorogenic enzyme to yield fluorescent product for a time between 5 and 240 minutes;
   (d) Measuring the fluorescence level in the solution; and
   (e) determining the amount of allergen specific IgE in the serum by comparing the fluorescence level determined in step d with those of control solutions.

2. The method of claim 1 wherein the insoluble support is a microtiter plate made of opaque material.

3. The method of claim 1 wherein the anti-IgE antibody is a monoclonal antibody.

4. The method of claim 1 wherein the microtiter plate is polystyrene or a styrene-(vinyl monomer) copolymer.

5. The method of claim 1 wherein the patient serum is removed from the insoluble support in step (a) by rinsing with a phosphate buffered solution having a pH within the range of from 6 to 8 and containing a non-ionic surfactant.

6. The method of claim 1 wherein the unconjugated anti-IgE antibody is removed from the insoluble support in step (b) with a phosphate buffered solution having a pH within the range of from 6 to 8 and containing a non-ionic surfactant.

7. The method of claim 1 wherein the allergen is derived from a pollen, mold, smut, animal dander or epidermal, insect, insect venom, dust, or food.

8. The method of claim 1 comprising
   (a) contacting an opaque polystyrene or styrene-(vinyl monomer) copolymer support having an allergen-soluble protein conjugate adhering thereto with patient serum for a sufficient time to permit conjugation of allergen specific IgE thereto;
   (b) romoving residual patient serum from the support;
   (c) contacting the support with an anti-IgE antibody labeled with a fluorogenic enzyme in an aqueous solution containing polyethylene glycol and a non-ionic surfactant for a time between 30 and 180 minutes and sufficient to permit conjugation of anti-IgE antibody to any allergen specific IgE conjugated to the support;
   (d) removing residual aqueous solution from step (c) from the support;
   (e) contacting the support with a solution of a substrate which undergoes reaction in the presence of the fluorogenic enzyme to yield fluorescent product for a time between 5 and 240 minutes; and
   (f) measuring the fluorescence level of the solution.

9. The method of claim 1 wherein the anti-IgE antibody is labeled with alkaline phosphatase.

10. The method of claim 9 wherein the substrate is 4-methyl-umbelliferyl phosphate.

11. The method of claim 1 wherein the aqueous solution contains from 0.01 to 0.1 wt.% of a non-ionic surfactant.

12. The method of claim 11 wherein the non-ionic surfactant is octylphenoxypolyethoxyethanol.

13. The method of claim 1 wherein the allergen conjugate adheres to the insoluble support by non-covalent binding.

14. The method of claim 13 wherein the allergen adhering to the insoluble support is a covalently bonded conjugate of the allergen and a soluble animal protein.

15. The method of claim 13 wherein the allergen is a covalently bonded conjugate of the allergen and bovine serum albumin.

16. The method of claim 13 wherein the allergen is covalently bonded to the bovine serum albumin with a carbodiimide.

17. A method for identifying and quantifying allergen specific IgE levels in patient serum comprising
   (a) Contacting an insoluble support having a covalently bonded conjugate of an allergen and a soluble animal protein adhering thereto, with patient serum for a sufficient time to permit conjugation and removing the patient serum therefrom;
   (b) Contacting the insoluble support with anti-IgE antibody labeled with a fluorogenic enzyme for a time between 30 and 180 minutes and sufficient to permit conjugation and removing unconjugated anti-IgE antibody therefrom;
   (c) Contacting the insoluble support with a solution of a substrate which undergoes reaction in the presence of the fluorogenic enzyme to yield fluorescent product for a time between 5 and 240 minutes; and
   (d) Measuring the fluorescence level in the solution, wherein the insoluble support is prerinsed with an aqueous buffered solution containing from 0.0001 to 0.5 wt. % of the animal protein before being contacted with patient serum.

18. The method of claim 17 wherein the soluble animal protein is bovine serum albumin.

19. The method of claim 18 wherein the allergen is covalently bonded to the bovine serum albumin with a carbodiimide.

20. The method of claim 18 wherein the allergen is covalently bonded to the bovine serum albumin with a bifunctional crosslinking agent.

* * * * *